(12) United States Patent
Sugano et al.

(10) Patent No.: US 10,440,346 B2
(45) Date of Patent: Oct. 8, 2019

(54) MEDICAL VIDEO DISPLAY SYSTEM

(71) Applicant: Medi Plus Inc., Tokyo (JP)

(72) Inventors: Naoya Sugano, Tokyo (JP); Minsu Kwon, Tokyo (JP)

(73) Assignee: MEDI PLUS INC., Tokyo (JP)

(*) Notice: Subject to any disclaimer, the term of this patent is extended or adjusted under 35 U.S.C. 154(b) by 0 days.

(21) Appl. No.: 15/711,334

(22) Filed: Sep. 21, 2017

(65) Prior Publication Data

US 2018/0098049 A1    Apr. 5, 2018

(30) Foreign Application Priority Data

Sep. 30, 2016  (JP) .................................. 2016-193722
Jul. 3, 2017   (JP) .................................. 2017-130412

(51) Int. Cl.
*G09G 5/00*      (2006.01)
*H04N 13/194*    (2018.01)
(Continued)

(52) U.S. Cl.
CPC ........... *H04N 13/194* (2018.05); *A61B 1/045* (2013.01); *A61B 90/361* (2016.02);
(Continued)

(58) Field of Classification Search
CPC ............. G06F 3/1454; G06F 17/30056; G06F 2203/04808; G06F 3/0484; G06F 3/041–04897; G09G 5/12; H04L 65/00–80; G09B 5/00–14; H04N 7/15–157; H04N 13/156; H04N 13/194;
(Continued)

(56) References Cited

U.S. PATENT DOCUMENTS 9,635,313 B2    4/2017  Hasegawa et al.
2010/0031202 A1* 2/2010 Morris ................ G06F 3/04883
                                                    715/863

(Continued)

FOREIGN PATENT DOCUMENTS

JP    10-98708 A      4/1998
JP    H11-136577 A    5/1999
(Continued)

OTHER PUBLICATIONS

Office Action dated Jan. 30, 2018, issued in corresponding Japanese Patent Application No. 2017-130412.
(Continued)

*Primary Examiner* — Stephen G Sherman
*Assistant Examiner* — Aaron Midkiff
(74) *Attorney, Agent, or Firm* — Westerman, Hattori, Daniels & Adrian, LLP

(57) ABSTRACT

Disclosed is a medical video display system with improved operability in manipulation regarding display of medical videos, which include a changeover device through which one, or two or more surgical videos are entered; and a work station and a distribution device control unit that distribute one video entered through the changeover device and display it on each of a touch panel and a monitor, wherein the work station allows the touch panel, having the video displayed thereon, to display an operation screen or an operation icon for accepting an operation directed to the monitor.

7 Claims, 13 Drawing Sheets

(51) Int. Cl.
  *A61B 90/00* (2016.01)
  *A61B 1/045* (2006.01)
  *H04N 13/156* (2018.01)
  *A61B 1/00* (2006.01)

(52) U.S. Cl.
  CPC ........ *H04N 13/156* (2018.05); *A61B 1/00009* (2013.01); *G06T 2210/41* (2013.01)

(58) Field of Classification Search
  CPC .... H04M 3/567; A61B 1/00009; A61B 1/045; A61B 90/361; G06T 2210/41
  USPC ........... 715/730, 753; 345/2.1–2.3, 173–178; 178/18.01–20.04
  See application file for complete search history.

(56) References Cited

U.S. PATENT DOCUMENTS

| | | | | |
|---|---|---|---|---|
| 2010/0093399 | A1* | 4/2010 | Kim | H04M 1/0202 455/566 |
| 2013/0019188 | A1 | 1/2013 | Hasegawa et al. | |
| 2015/0062048 | A1* | 3/2015 | Park | G06F 3/1423 345/173 |
| 2015/0199164 | A1* | 7/2015 | Moore | G06F 3/1454 345/1.1 |
| 2017/0185272 | A1 | 6/2017 | Hasegawa et al. | |

FOREIGN PATENT DOCUMENTS

| | | |
|---|---|---|
| JP | 2000165787 A | 6/2000 |
| JP | 2004-195252 A | 7/2004 |
| JP | 2004-312468 A | 11/2004 |
| JP | 2005-323887 A | 11/2005 |
| JP | 2013-020520 A | 1/2013 |

OTHER PUBLICATIONS

Office Action dated Oct. 17, 2017, issued in Japanese Patent Application No. 2017-130412.

Document submitted with Japan Patent Office dated Oct. 21, 2016 in order to apply an exception of loss of novelty under Article 30 of Japan Patent Law, which was submitted in Japanese Patent Application No. 2016-193722, w/ English concise explanation (3 pages).

* cited by examiner

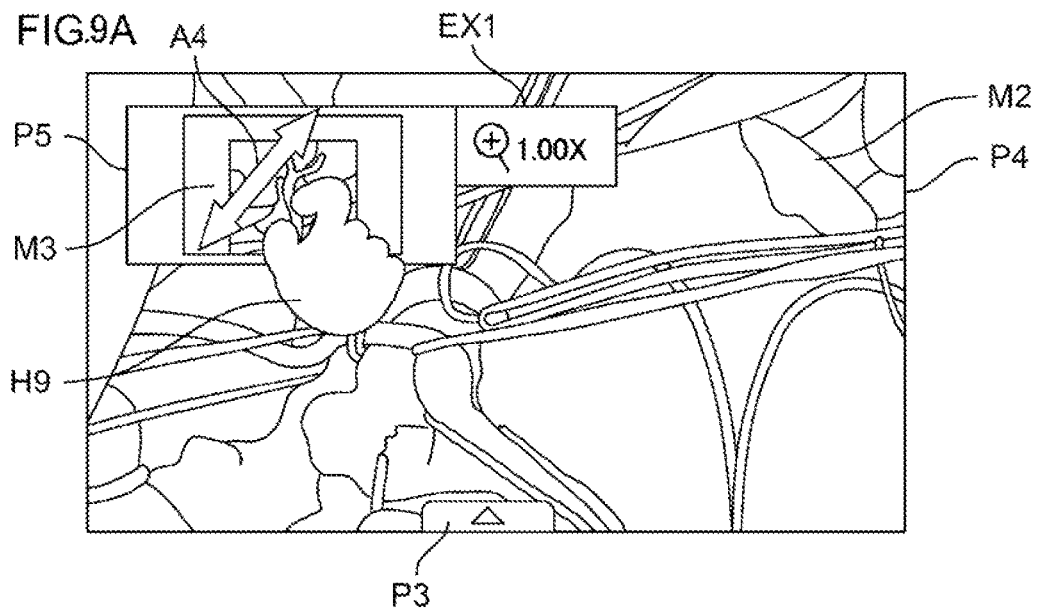
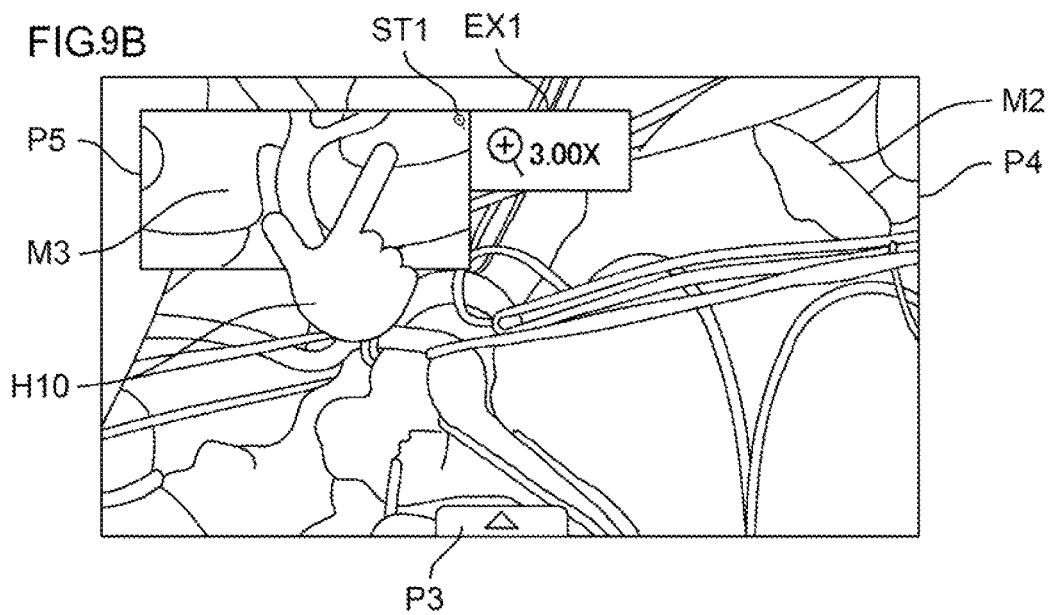

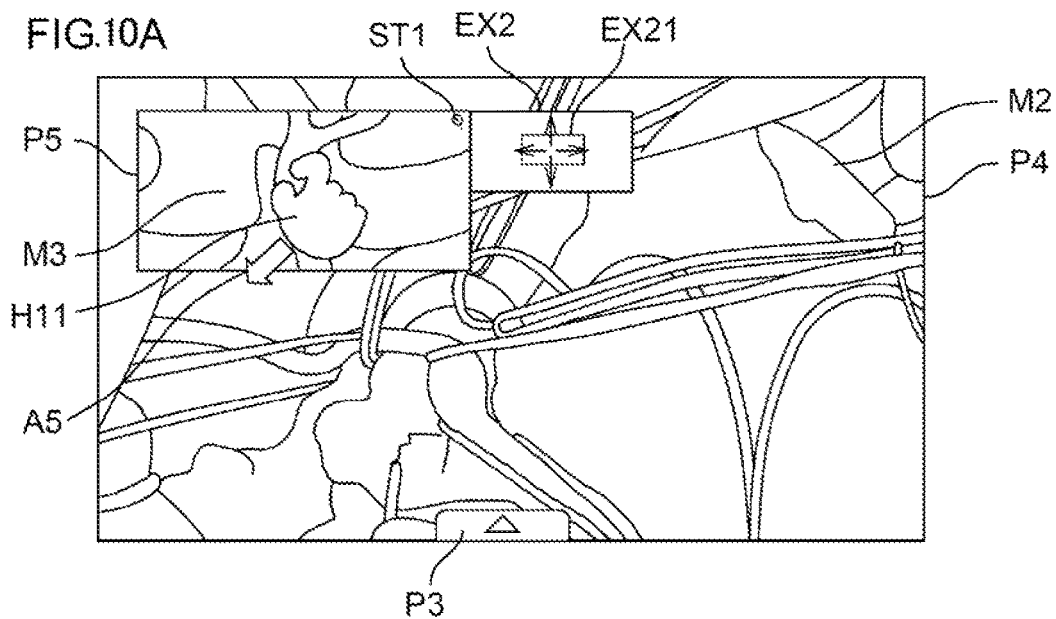
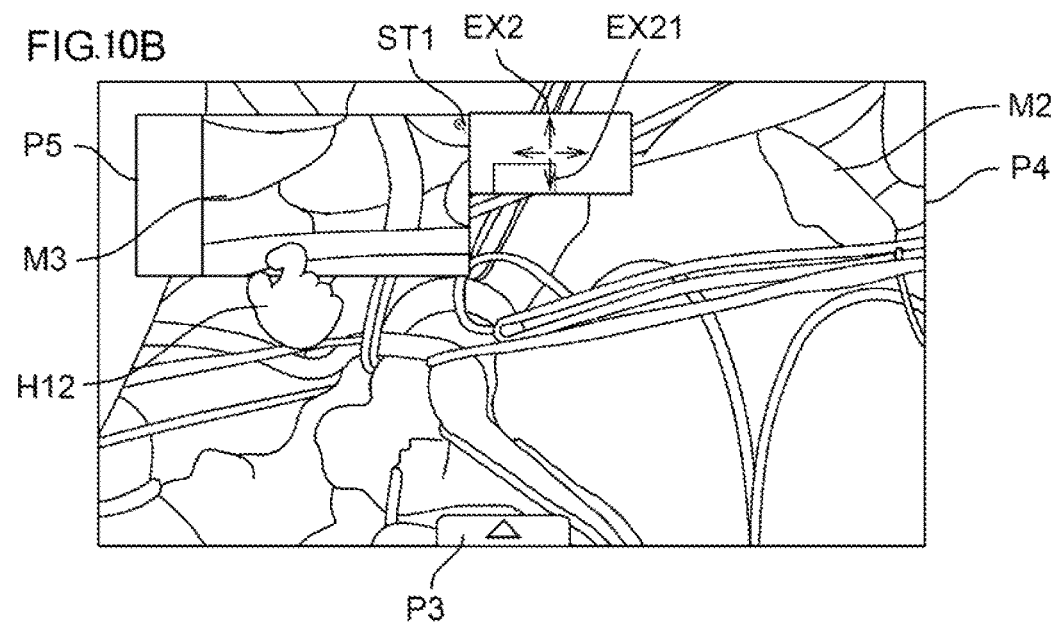

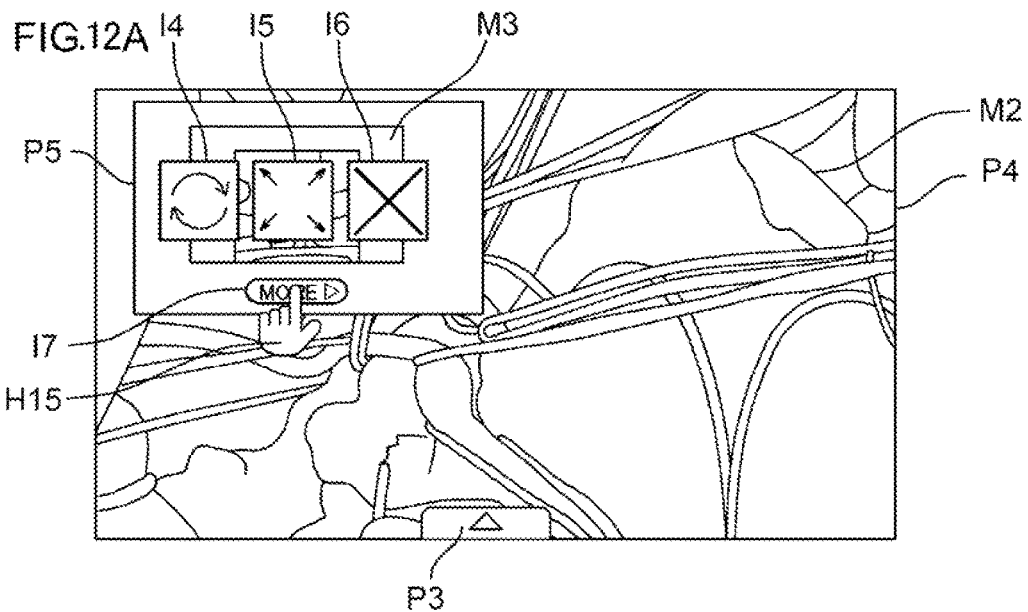
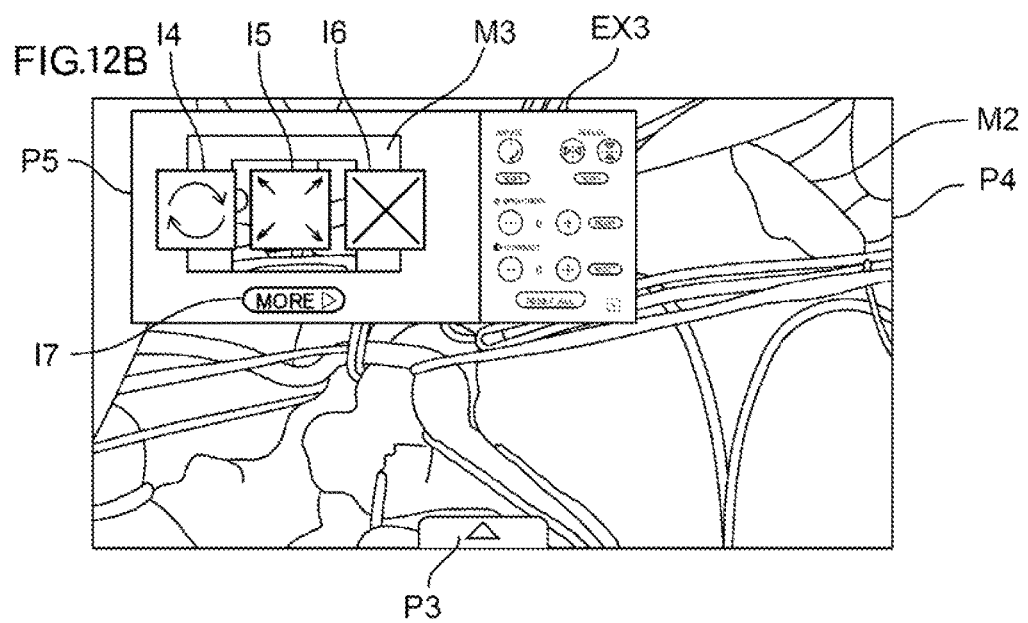

MEDICAL VIDEO DISPLAY SYSTEM

CROSS-REFERENCE TO RELATED APPLICATIONS

This application claims the benefit of Japanese Patent Applications No. 2016-193722 filed on Sep. 30, 2016 and No. 2017-130412 filed on Jul. 3, 2017 in the Japanese Patent Office, the disclosure of which is herein incorporated in its entirety b reference.

BACKGROUND

This invention relates to a medical Video display system.

In recent fields of surgery including endoscopic surgery, there are a variety of methodologies by which surgery is conducted not only by observing affected areas by bare eyes, but also by viewing a video that is captured by an imaging device pertaining to medical equipment, and displayed on a monitor.

In this sort of surgery, two or more modes of capturing images of affected areas may occasionally be used, needing suitably charging the videos to be output to the monitor. In some cases, the videos thus captured during surgery are recorded for use in clinical studies and so forth.

Techniques of this sort have been described, for example, in JP-A-1110-98708 and JP-A-2004-312468.

JP-A-1110-98708 discloses a device that includes a matrix switch for selecting and changing video signals, and an on-screen controller for superposing a title signal representing character, figure and so forth on the selected video signal. More specifically this device is characterized by its ability to select and change the matrix switch, and at the same time, to change display on the on-screen controller.

JP-A-2004-312468 describes a video system used for surgery, by which endoscopic video signal and ultrasonic video signal can respectively be played back on different monitors, or recorded in different recorders. This device is characterized in that it has a discrimination unit that discriminates types of video equipment (cameras) whose video signals were output on a group of monitors, by receiving specific information from such video equipment, making it possible to display the state of connection of the plurality of video equipment.

SUMMARY

The prior art device and system described in JP-A-H10-98708 and JP-A-2004-312468 have, however, suffered from poor operability, and have required a certain level of skill for proper manipulation.

This invention was conceived in consideration of the problem, and is to provide a medical video display system with an improved operability for displaying medical videos.

According to this invention, there is provided a medical video display system that includes an entry unit through which one, or two or more surgical videos are, entered; and control unit that distributes one video entered through the entry unit and displays it on each of a touch panel and a monitor, the control unit allows the touch panel, having the video displayed thereon, to display an operation screen or an operation icon for accepting an operation directed to the monitor.

According to this invention, it now becomes possible to suitably operate, but without viewing, a video being displayed on the monitor, only by viewing a video being displayed on the touch panel.

BRIEF DESCRIPTION OF THE DRAWINGS

The above and other objects, advantages and features of the present invention will be more apparent from the following description of a certain preferred embodiment taken in conjunction with the accompanying drawings, in which:

FIGS. 9A and 9B are schematic drawings illustrating a method of manipulation on the touch panel.

FIGS. 10A and 10B are schematic drawings illustrating a method of manipulation on the touch panel.

FIGS. 12A and 12B are schematic drawings illustrating a method of manipulation on the touch panel.

DETAILED DESCRIPTION

An embodiment of this invention will be explained below, referring to the attached drawings. In these drawings, all similar constituents will have the same reference sings, so as to suitably avoid repetitive explanation.

<Constituents Contained in Medical Video Display System 100>

Figure 1:
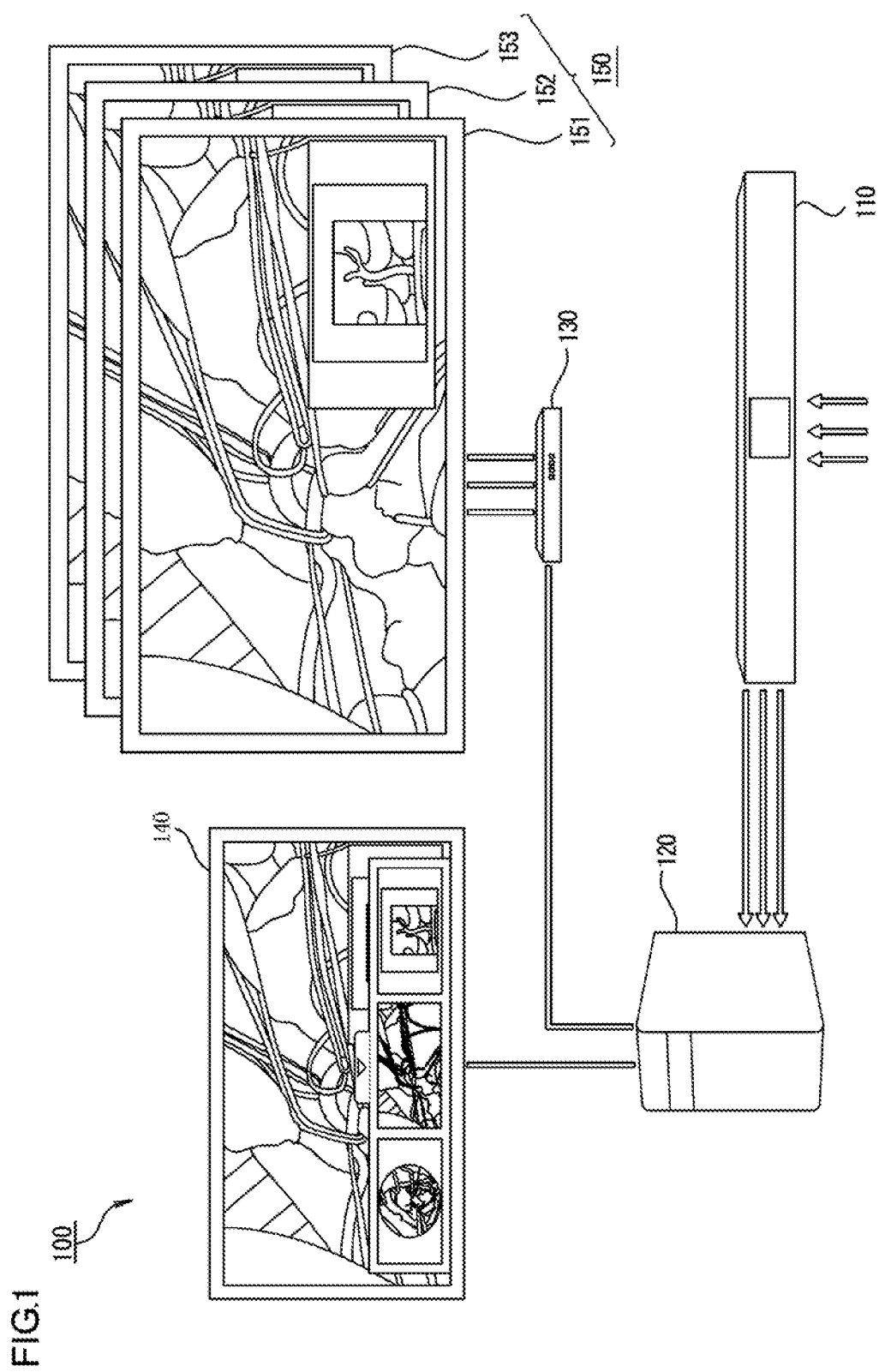
FIG. 1 is a medical video display system according to an embodiment of this invention.

First, components contained in a medical video display system 100 will be explained refining to FIG. 1. FIG. 1 is a drawing illustrating a medical video display system 100 according to this embodiment.

Arrows in FIG. 1 point sources and destinations of videos transferred among the individual components. The arrows are therefore not always required to agree with actual send/receive operations.

The medical video display system 100 has a changeover device 110, a work station 120, a distribution device 130, a touch panel 140, and a plurality of monitors 150 (first monitor 151, second monitor 152, and third monitor 153).

The changeover device 110 functions as an entry unit through which one, or two or more surgical videos are entered.

The work station 120 and the distribution device 130 cooperatively function as the control unit that distributes one video entered through the changeover device 110 and displays it on each of the touch panel 140 and the monitor 150, and, allows the touch panel 140, having the video displayed thereon, to display an operation screen or an operation icon for accepting an operation directed to the monitor 150.

Now the "video" means a set of still images that continuously change, which are successively played back as if a pictured object is moving. This is synonymous to "movie".

What is called "video" in the description regarding the embodiment may include file data (moving picture data) displayed as video, after suitably processed, on the touch panel 140 and the monitor 150:

The "surgical video" means videos regarding surgery performed as a medical action. Specific examples of the "surgical video" include videos captured by an imaging device pertaining to medical equipment such as endoscope, and videos output from a measuring instrument that measures the state of a patient.

Now "distributes one video" means that one video is output to a plurality of destinations. For example, this applies to an event in which a video captured by an endoscope (not illustrated) is entered into the work station 120, and the work station 120 then outputs acts the entered video to each of the touch panel 140 and the monitor 150. This alternatively applies to an event in which video is entered through the work station 120 into the distribution device 130, and the distribution device 130 then outputs the entered video to each of the first monitor 151, the second monitor 152 and the third monitor 153.

When "distributing one video", the same output format, or different output formats may be used for a plurality of destinations. For example, the work station 120 in this embodiment employs a high-definition multimedia interface (HDMI) as the output format both for the touch panel 140 and the monitor 150. It suffices that the output format described above is a mere example. The output format may suitably be determined depending, for example, on specification of the destination.

The changeover device 110 functions to accept entry of surgical videos, and to select and change videos to be displayed on the touch panel 140 and the monitor 150, among the thus entered videos. This function is also called "switching". The videos to be displayed on the touch panel 140 and the monitor 150 are selected through an operation screen P3 or operation icons I1 to I6 displayed on the touch panel 140, details of which will be given later.

The work station 120 outputs the video to each of the touch panel 140 and the monitor 150, while keeping them in synchronization. The "synchronization" means that both displayed videos change at the same time, but allowing a time lag due to process delay on each component.

The work station 120 functions to change a display mode of the touch panel 140 and the monitor 150 in response to operations accepted by the touch panel 140, and to send a request to the changeover device 110 to output the selected video.

The distribution device 130 functions to distribute the video output from the work station 120 to plurality of monitors 150.

The touch panel 140 is an electronic device having a display device and a locater device combined therein. The touch panel 140 functions to display the video output from the work station 120, and to accept an operation by recognizing a display position touched by an operator, and a way of touching.

The monitor 150 is a display device, and functions to display the video output from the work station 120. The monitor 150 in this embodiment is a collective term for the first monitor 151, the second monitor 152 and the third monitor 153.

The size and weight of the touch panel 140 are preferably smaller than those of the monitor 150. The touch panel 140 is preferably portable to the close vicinity of the operator since the device is intuitively manipulable by the operator who watches thereon the video, meanwhile, the monitor 150 is only good enough to be installable at a place where it is easily recognizable, and is less necessarily portable as compared with the touch panel 140.

The monitor 150 preferably has a display area larger than that of the touch panel 140. This is because the touch panel 140 is good enough to be recognizable by an operator, whereas display on the monitor 150 is preferably viewable by a plurality of surgical staffs.

Note, however, that the size and weight of the touch panel 140 and the monitor 150 may suitably be selectable depending on an environment where the medical video display system 100 is used, even allowing that the touch panel 140 and the monitor 150 will have equivalent sizes and/or weights.

<Displays on Touch Panel 140 and Monitor 150, and manipulation of Displays>

Next, displays on the touch panel 140 and the monitor 150, and manipulation of the displays will be explained referring to FIG. 2A to FIG. 13.

Figure 2A:
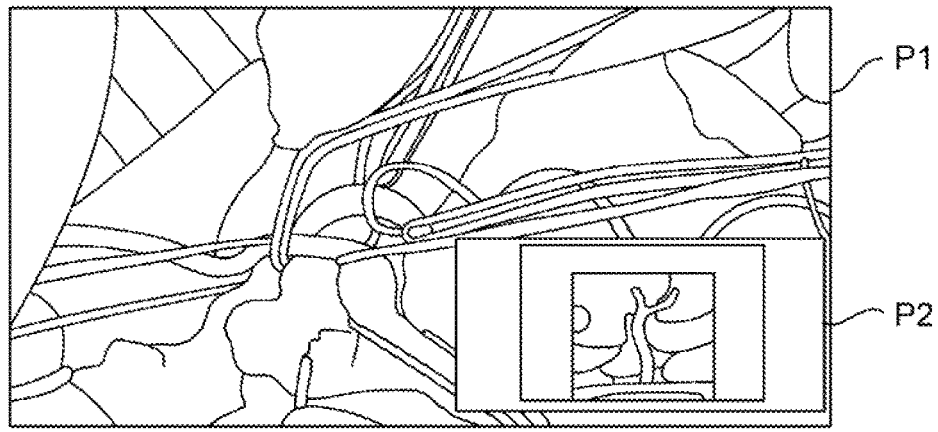
FIGS. 2A to 2C are drawings illustrating specific examples of a display screen of a touch panel and a display screen of a monitor.
Figure 2B:
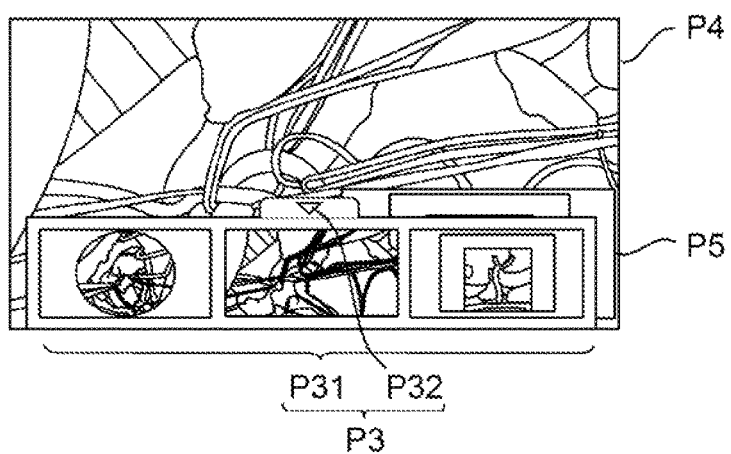
Figure 2C:
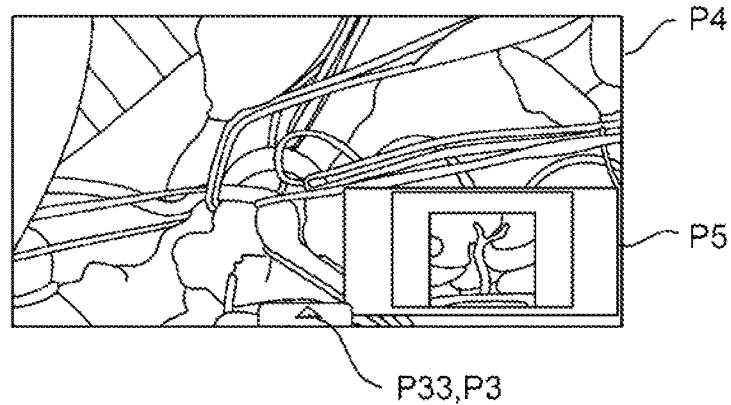
Figure 13:
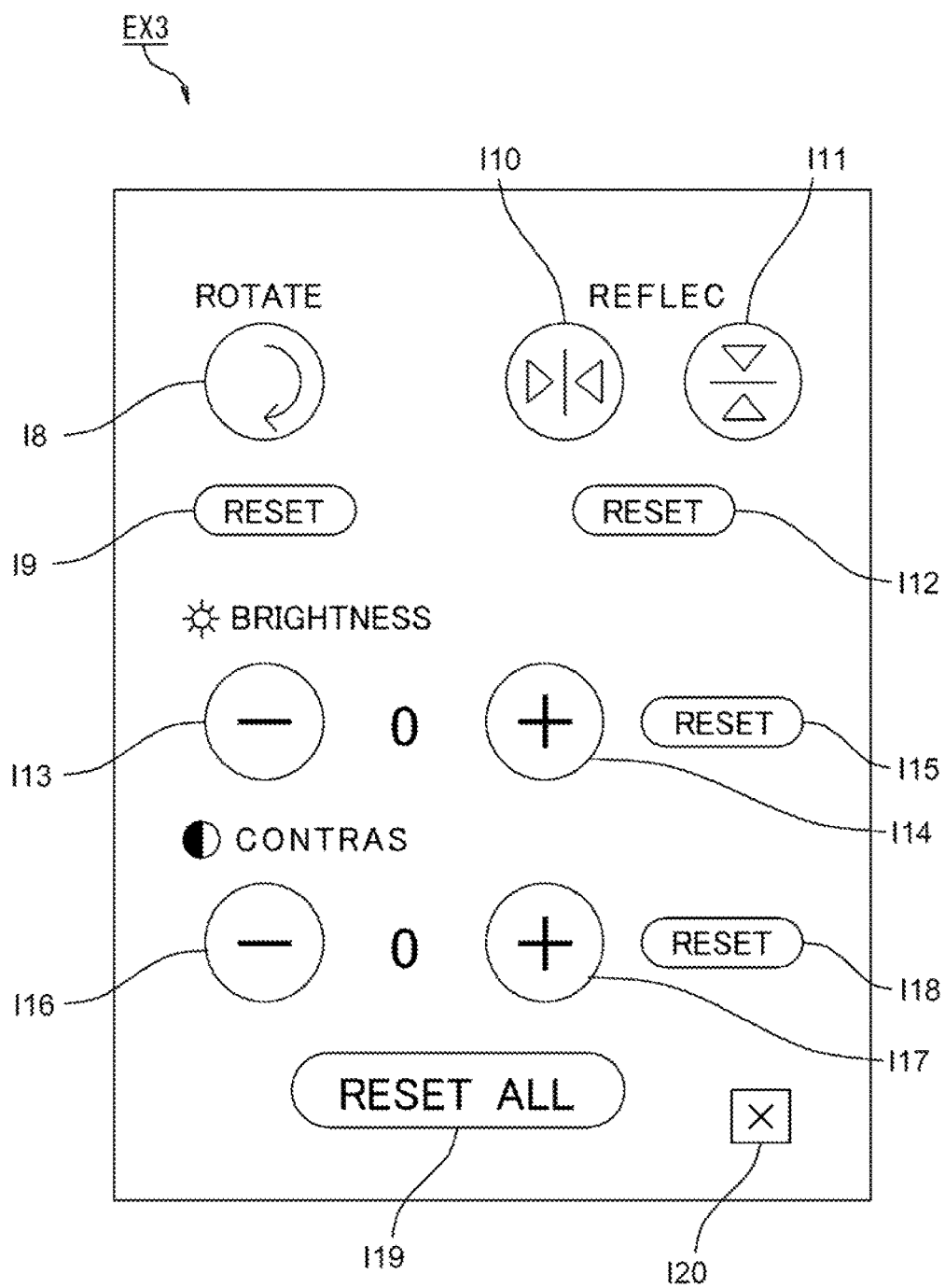
FIG. 13 is an enlarged vie illustrating a zoom-in panel.

FIGS. 2A to 2C are drawings illustrating one specific example of a display screen of the touch panel 140 and a display screen of the monitor 150. FIGS. 3A to 3D are drawings illustrating one specific example of a separation style of the display screen of the monitor 150. FIG. 4A to FIG. 12B are schematic drawings for explaining how to manipulate the touch panel 140. FIG. 13 is an enlarged view of a zoom-in panel EX3.

In the example illustrated in FIGS. 2A to 2C, the display screen of the monitor 150 contains a main screen P1 and a sub-screen P2, and the display screen of the touch panel 140 contains an operation screen P3, a main screen P4 and a sub-screen P5.

FIG. 2A illustrates one scene at a certain point in time, where different videos are displayed on the main screen P1 and the sub-screen P2 of the monitor 150. As illustrated in FIG. 2A, the sub-screen P2 is overlaid on the main screen P1.

Figure 3A:
FIGS. 3A to 3D are drawings illustrating a specific example of division formats regarding the display screen of the monitor.
Figure 3B:
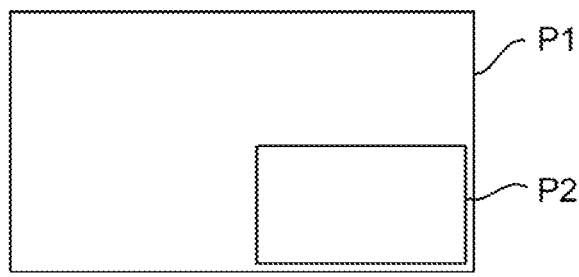
Figure 3C:
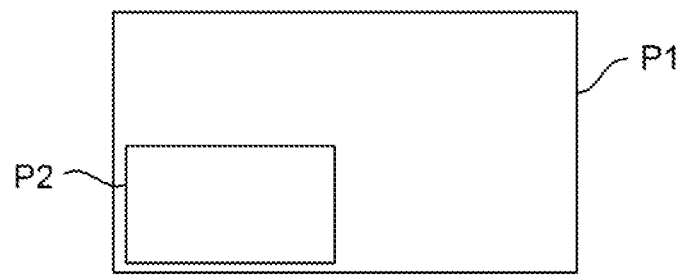
Figure 3D:
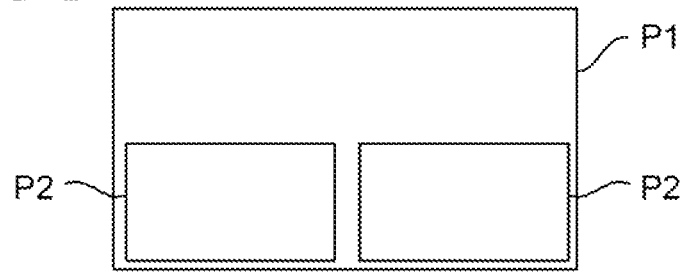

FIGS. 3A to 3D illustrate exemplary layouts of the main screen P1 and the sub-screen P2 on the display screen of the monitor 150. FIG. 3A illustrates an exemplary layout where the display screen of the monitor 150 is used solely for the main screen P1 (full-screen). FIG. 3B illustrates an exemplary layout where the main screen P1 is displayed over the entire display screen of the monitor 150, with the sub-screen P2 overlaid on the right lower portion of the main screen P1. FIG. 3C illustrates an exemplary layout Where the main screen P1 is displayed over the entire display screen of the monitor 150, with the sub-screen P2 overlaid on the left lower portion of the main screen P1. FIG. 3D illustrates an exemplary layout where the main screen P1 is displayed over the entire display screen of the monitor 150, with the sub-screens P2 overlaid both on the right and left lower portions of the main screen P1, that is, an exemplar layout having two sub-screens P2 overlaid on one main screen P1.

Note that the embodiment of this invention is not limited to the layouts illustrated in FIGS. 3A to 3D. For example, three or more sub-screens P2 may be overlaid on the main seen P1, or the entire display screen of the monitor 150 may be equally divided solely by the sub-screens P2 (bisection, quadrisection, etc.).

FIG. 2B illustrates a scene where a video synchronized with the main screen P1 at this point in time is displayed on the main screen P4 of the touch panel 140, and, a video synchronized with the sub-screen P2 at this point in time is displayed on the sub-screen P5 of the touch panel 140. FIG. 2B illustrates a scene where the operation screen P3 is zoomed in on the touch panel 140.

FIG. 2C illustrates a scene where a video synchronized with the main screen P1 at this point in time is displayed on the main screen P4 of the touch panel 140, and, a video synchronized with the sub-screen P2 at this point in time is displayed on the sub-screen P5 of the touch panel 140. FIG. 2C illustrates a scene where the operation screen P3 is zoomed out on the touch panel 140.

Figure 4A:
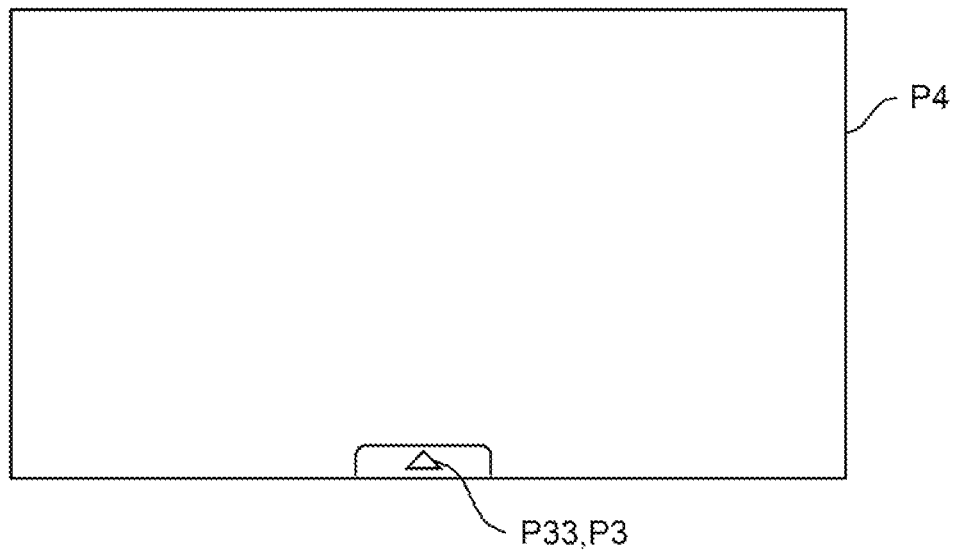
FIGS. 4A and 4B are schematic drawings illustrating a method of manipulation on the touch panel.
Figure 4B:
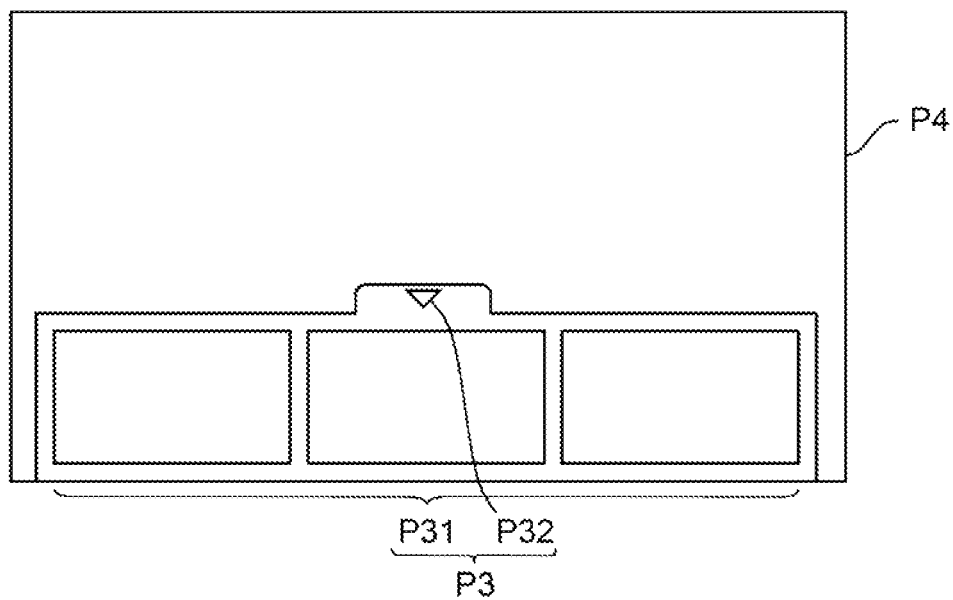

As illustrated in FIG. 4A, the operation screen P3, being zoomed out, has an up-pointing indicator P33 at the lower center portion thereof. Upon touching the up-pointing indicator P33, the operation screen P3 is zoomed in. As illustrated in FIG. 4B, operation screen P3, being zoomed in, has a down-pointing indicator P32 at the upper center portion thereof. Upon touching the down-pointing indicator P32, the operation screen P3 is zoomed out.

The operation screen P3 displayed on the touch panel 140 contains a thumbnail P31 of the videos entered through the changeover device 110. In other words, the operation screen P3 will have displayed thereon all videos entered through the changeover device 110, regardless of whether the operator selected any of them or not.

The work station 120 allows the touch panel 140 to display thereon a video that is selected, by a touch operation accepted by the touch panel 140, from the videos contained in the thumbnail P31, separately from the thumbnail P31, and also allows the monitor 150 to display the selected video.

The thumbnail is a list of videos. In this embodiment, all videos entered through the changeover device 110 are made viewable, without omission, in the thumbnail P31 on the operation screen P3, where each video is synchronized with the videos displayed car the main screen P1 and the sub-screen P2. Such embodiment is, however, a mere example. Each video displayed on the thumbnail P31 on the operation screen P3 may have a content just enough to gasp a point thereof (the opening part or title of the video, etc.)

Although FIG. 2B and some other drawings illustrate exemplary screens where the thumbnail P31 contains three videos, the number of videos includable in the thumbnail P31 may suitably be increased or decreased.

As illustrated in FIG. 2B, depending on a layout of the main screen P4 and the sub-screen P5 on the touch panel 140, the videos displayed on the main screen P4 and the sub-screen P5 would be hidden by the operation screen P3 overlaid thereon. As a solution, the display of the operation screen P3 is preferably transparent to some degree. With such solution, the videos displayed on the main screen P4 and the sub-screen P5 will be viewable, even if the main screen P4 and the sub-screen P5 are overlaid with the operation screen P3.

Figure 5A:
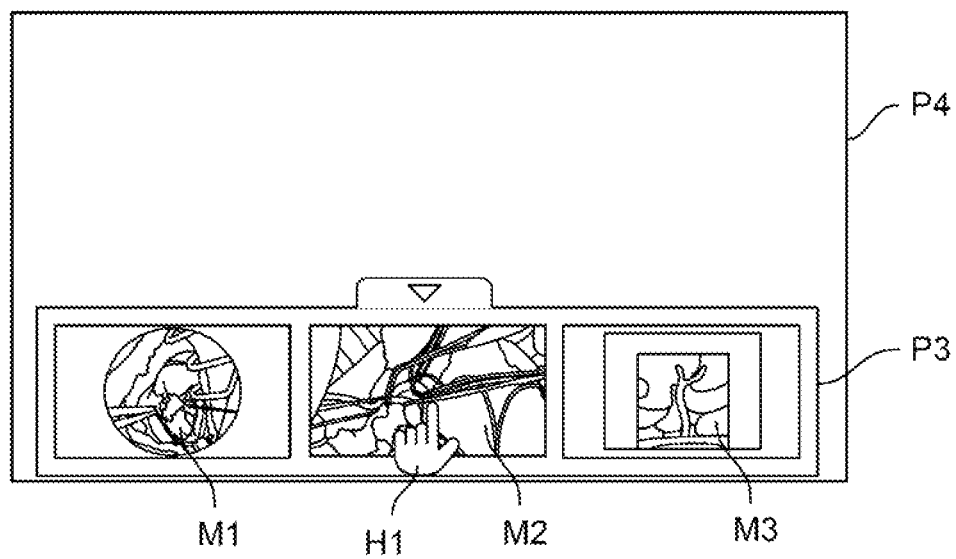
FIGS. 5A and 5B are schematic drawings illustrating a method of manipulation on the touch panel.
Figure 5B:
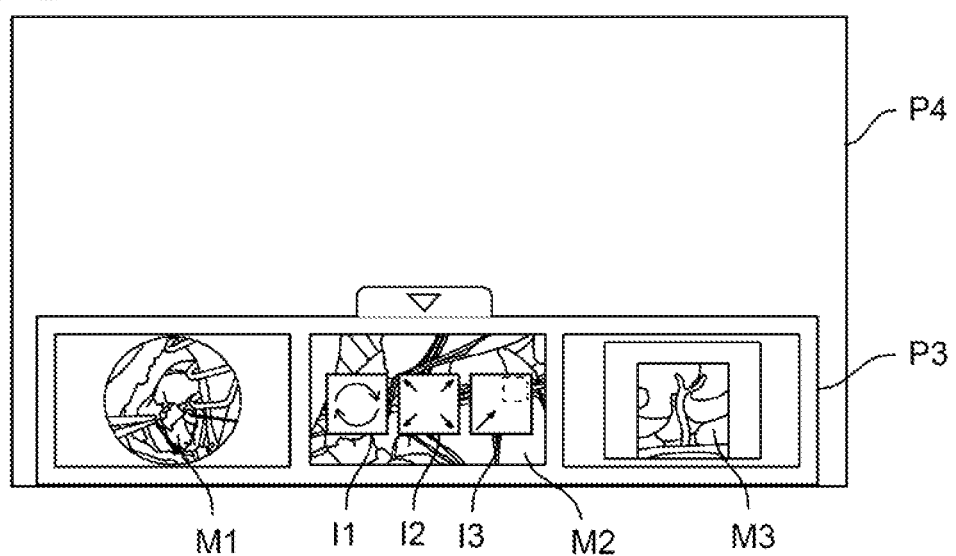

Manipulation for selecting the video displayed on the operation screen P3 (thumbnail P31) will further be detailed referring to FIGS. 5A and 5B. Note that a finger-shaped pointer illustrated in FIG. 5A conveniently represents an action of touching by the operator, and does not appear on the actual screen of the touch panel 140. The same will apply to finger-shaped pointers H2 to H8 in the description below.

For example, given that the operation screen P3 has displayed therein video M1, video M2 and video M3, and the operator touched the video M2 once (see FIG. 5A). The work station 120 then allows the touch panel 140 to display operation icon I1, operation icon I2 and operation icon I3, so as to be overlaid on the video M2 (see FIG. 5B).

When the operation icon I1 is touched, the work station 120 allows the main screen P4 to replace the video being displayed thereon with the video M2, to thereby display the video M2 on the main screen P4.

When the operation icon I2 is touched, the work station 120 allows the main screen P4 to display the video M2 to full screen, regardless of the display mode of the main screen P4.

When the operation icon I3 is touched, the work station 120 allows the touch panel 140 to newly create the sub-screen P5 so as to be overlaid on the main screen P4, and to display the video M2 on the sub-screen P5. The position where the sub-screen P5 is created may preliminarily be set, typically as illustrated previously in FIGS. 3A to 3D. If the sub-screen P5 has already been created, the work station 120 may allow the sub-screen P5 to replace the video, being displayed thereon at this point in time, with the video M2, and to thereby display the video M2 on the sub-screen P5.

The operator can select the video listed in the operation screen P3 (thumbnail P31) alternatively by the operation below.

Figure 6A:
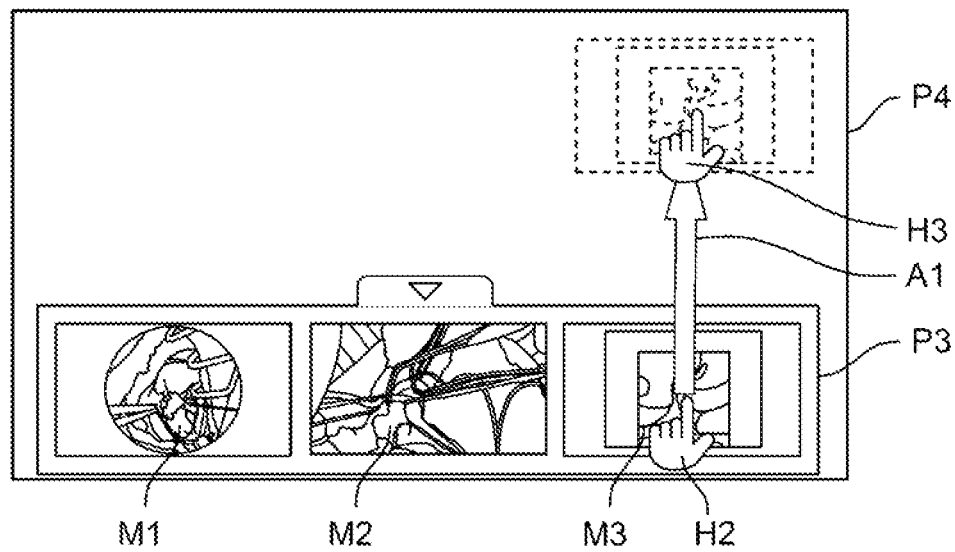
FIGS. 6A and 6B are schematic drawings illustrating a method of manipulation on the touch panel.
Figure 6B:
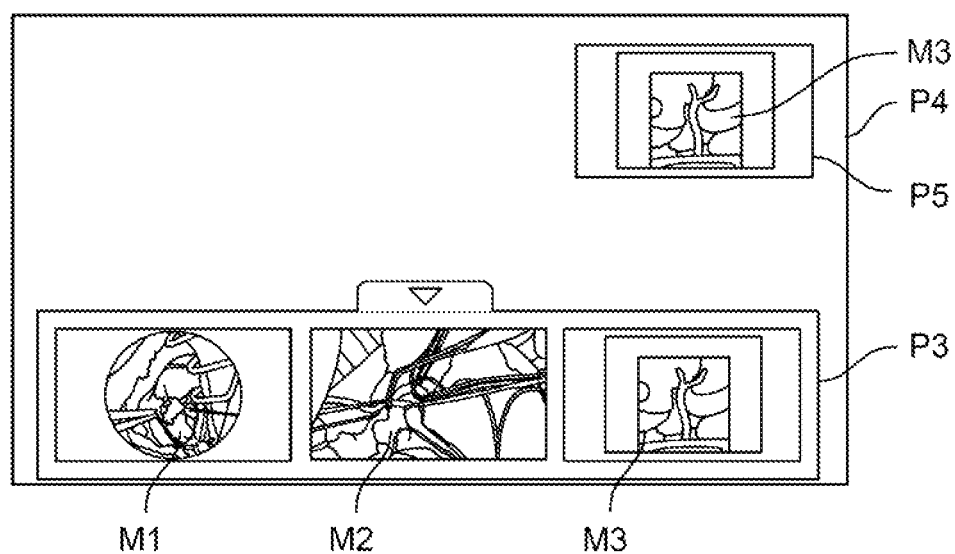

FIG. 6A illustrates an operation of moving the video M3, being displayed on the operation screen P3, to the main screen P4 (action depicted by an arrow A1 and a finger-shaped pointer H3), while keeping the video M3 touched (action depicted by a finger-shaped pointer H2). This sort of operation will be referred to as "drag operation" in this embodiment.

Upon acceptance of such operation by the touch panel 140, the work station 120 can create the sub-screen P5 at the position where the video M3 was dragged to, so as to be overlaid on the main screen P4, thereby displaying the video M3 on the sub-screen P5. Now, there can be seen on the display screen of the touch panel 140, as if the video M3 was moved firm the operation screen P3 to the sub-screen P5.

The drag operation may also be used in the process below.

Figure 7A:
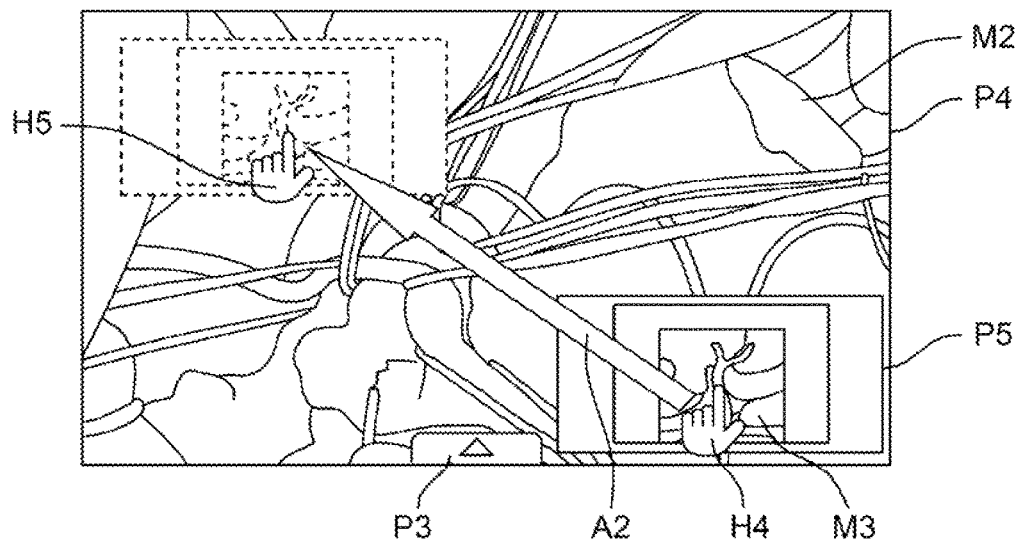
FIGS. 7A and 7B are schematic drawings illustrating a method of manipulation on the touch panel.

FIG. 7A illustrates an exemplary operation of moving the video M3, being displayed on the sub-screen P5, from the lower right portion to the upper left portion of the main screen P4 (action depicted by an arrow A2 and a finger-shaped pointer H5), while keeping the video M3 touched (action depicted by a finger-shaped pointer H4). Also this sort of operation will be referred to as "drag operation" in this embodiment.

Figure 7B:
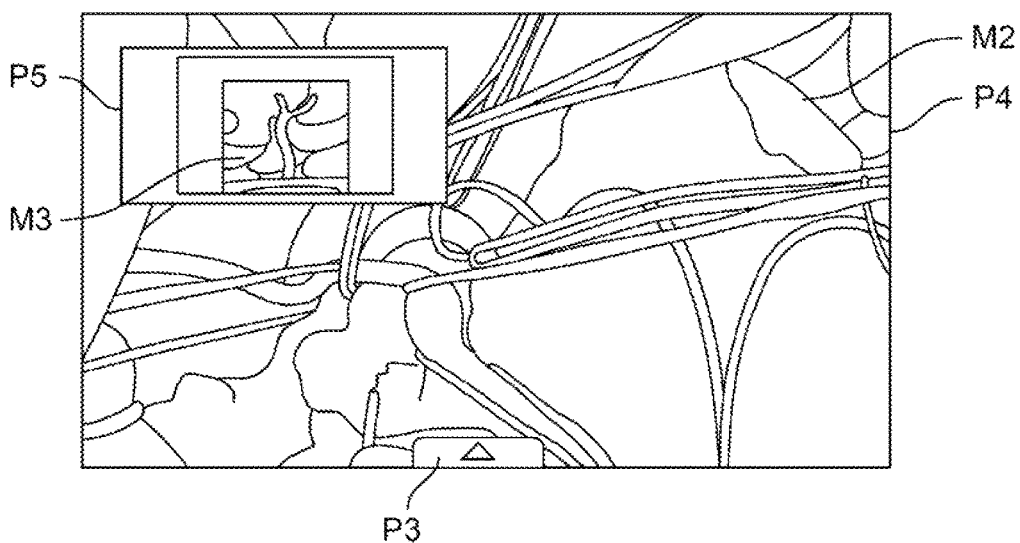

Upon acceptance of such operation by the touch panel 140, the work station 120 can move the display position of the sub-screen P5 (video M3) (see FIG. 7B).

To summarize, these two display processes based on the drag operation may be briefed as below.

That is, the work station 120 is designed to enable moving of the display position of the video, being displayed in a part of the display area of the touch panel 140, in response to the drag operation accepted by the touch panel 140. The work station 120 can also move the display position of video on the monitor 150, corresponding to the movement of the display position of video, in response to the drag operation accepted by the touch panel 140 (See, e.g., FIG. 2A and FIG. 2B).

The drag operation may also be used fir the process below.

Figure 8A:
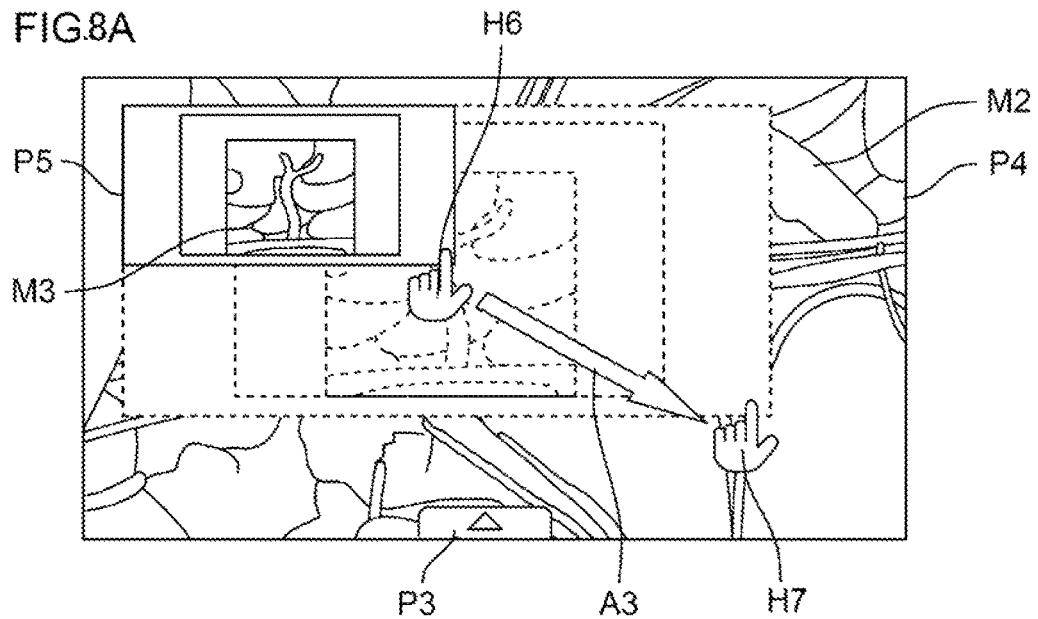
FIGS. 8A and 8B are schematic drawings illustrating a method of manipulation on the touch panel.

FIG. 8A illustrates an exemplary operation of moving a corner (or outer frame) of the sub-screen P5 outward (lower right direction in FIG. 8A) (action depicted by an arrow A3 and a finger-shaped pointer H7), while keeping the corner touched (action depicted by a finger-shaped pointer H6). Also this sort of operation will be referred to as "drag operation" in this embodiment.

Figure 8B:
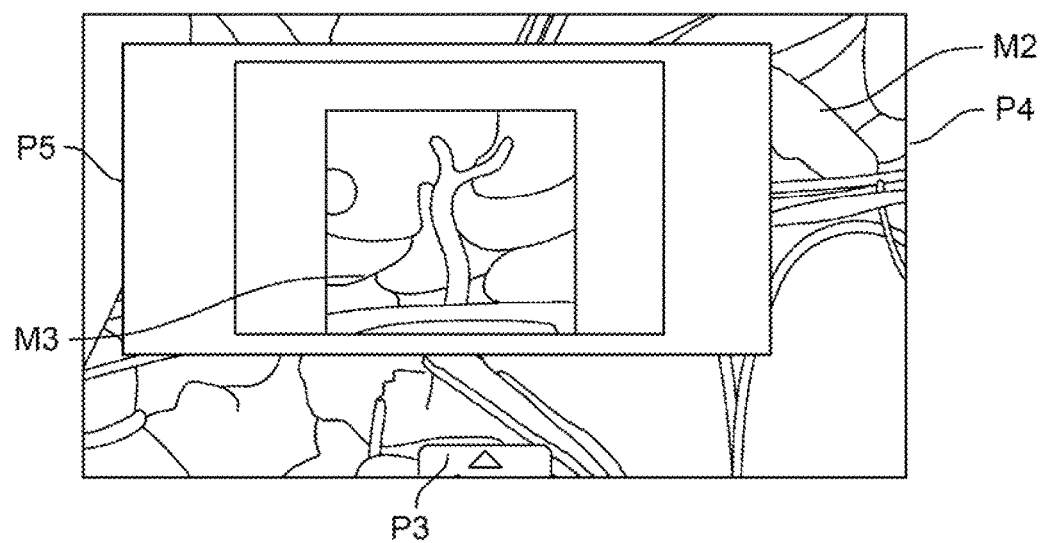

Upon acceptance of such operation by the touch panel 140, the work station 120 can allow the sub-screen P5 (video M3) to enlarge the outer frame thereof (see FIG. 8B).

Although not illustrated, when the touch panel 140 accepts an operation of moving a corner (or outer flame) of the sub-screen P5 inward the work station 120 can allow the sub-screen P5 to reduce the size thereof.

To summarize, these display processes based on the drag operation may be briefed as below.

The work station 120 is designed to enable enlargement or reduction of the video, being displayed in the display area of the touch panel 140, in response to the drag operation accepted by the touch panel 140. The work station 120 can also zoom in/out the video on the monitor 150, corresponding to the enlargement or reduction of video in response to the drag operation (Compare, e.g., FIG. 2A with FIG. 2B and FIG. 2C).

Upon acceptance of a pinch operation by the touch panel 140, the work station 120 enables a process below. Now the "pinch operation" means an operation activated by two fingers that are placed on two points in the display area of the touch panel 140, and are moved so as to widen or narrow the distance between the two points being touched.

FIG. 9A illustrates an exemplary pinch operation, in which two points in the display area of the sub-screen P5, having the video M3 displayed thereon, are touched and the distance between these two points is then widened (action depicted by an arrow A4 and a finger-shaped pointer H9).

Upon acceptance of the pinch operation by the touch panel 140, the work station 120 can allow the sub-screen P5 to zoom in a part of the video M3, while keeping the contour size thereof unchanged (see FIG. 9B). A finger-shaped pointer H10 illustrated in FIG. 9B depicts an operation of widening the distance between the two points being touched, from the distance specified by the finger-shaped pointer H9.

The touch panel 140 in this embodiment allows for zooming within the range from the actual scale up to three-fold magnification. The range is, however, an exemplary one, instead allowing magnification beyond three-fold, or reduction below the actual scale.

Upon acceptance of such pinch operation, a zoom-in panel EX1 is displayed beside the sub-screen P5, which contains a current magnification. For example, the zoom-in panel EX1 illustrated in FIG. 9A indicates that the video M3 is displayed in its actual scale at this point in time. Meanwhile, the zoom-in panel EX1 illustrated in FIG. 9B indicates that the video M3 is displayed with three-fold magnification at this point in time.

When the video M3 is displayed on the sub-screen P5 at a magnification beyond the actual scale, in response to the pinch operation as described above, a status icon ST1 indicating that the video is being magnified appears at a corner of the sub-screen P5. This is an expedient for those who do not take part in the pinch operation (for example, viewers of the monitor 150 on which the video is displayed in synchronization with the touch panel 140), notifying that the video M3 is displayed in a magnification mode (not in the actual size).

Although the above description mating reference to FIGS. 9A and 9B dealt with the enlargement and reduction of the video M3, being displayed on the sub-screen P5, by the pinch operation, there may be another design in which the video M2, being displayed on the main screen P4, may be zoomed in/out by the same pinch operation.

Upon acceptance of the drag operation, with two points in the display area kept touched on the touch panel 140, the work station 120 can go into the process below.

FIG. 10A illustrates an exemplary operation of moving two touch points, which are given on the video M3 partially zoomed-in by the pinch operation, in the lower left direction (action depicted by an mow A5 and a finger-shaped pointer H11), while keeping the two points touched. Also this sort of operation will be referred to as "drag operation" in this embodiment.

Upon acceptance of such drag operation by the touch panel 140, the work station 120 can allow the sub-screen P5 to move the display position of the video M3 being displayed thereon. For example, the sub-screen P5, illustrated in FIG. 10A so as to display the center portion of the video M3, can now display the left lower portion of the video M3 as illustrated in FIG. 10B, as a result of acceptance of the drag operation described above. A finger-shaped pointer H12 in FIG. 10B depicts that the touch position has been moved to the left and downward from the touch position indicated by the finger-shaped pointer H11.

Upon acceptance of such pinch operation, a zoom-in panel EX2 is displayed beside the sub-screen P5, which contains a current display position of the video M3. For example, the zoom panel EX2 illustrated in FIG. 10A indicates that the center portion of the video M3 is displayed at this point in time, with the aid of a position teaching frame EX21 displayed at the center of the zoom-in panel EX2. Meanwhile, the zoom-in panel EX2 illustrated in FIG. 10B depicts that the display position of the video M3 has been moved to the left and downward, as a result of movement of the position teaching frame EX21 to the left and downward in the zoom-in panel EX2.

With such design, the display position of the video M3 is clearly taught also to those who do not take part in the drag operation (for example, viewers of the monitor 150 on which the video is displayed in synchronization with the touch panel 140).

Although the above description, making reference to FIGS. 10A and 10B, dealt with an exemplary case where the video M3 being displayed on the sub-screen P5 is moved by the drag operation, there may be another design in which the video M2, being displayed on the main screen P4, is movable by the same drag operation.

Upon acceptance of the rotating operation by the touch panel 140, with the display area thereof touched at two points, the work station 120 can go into the process below.

Figure 11A:
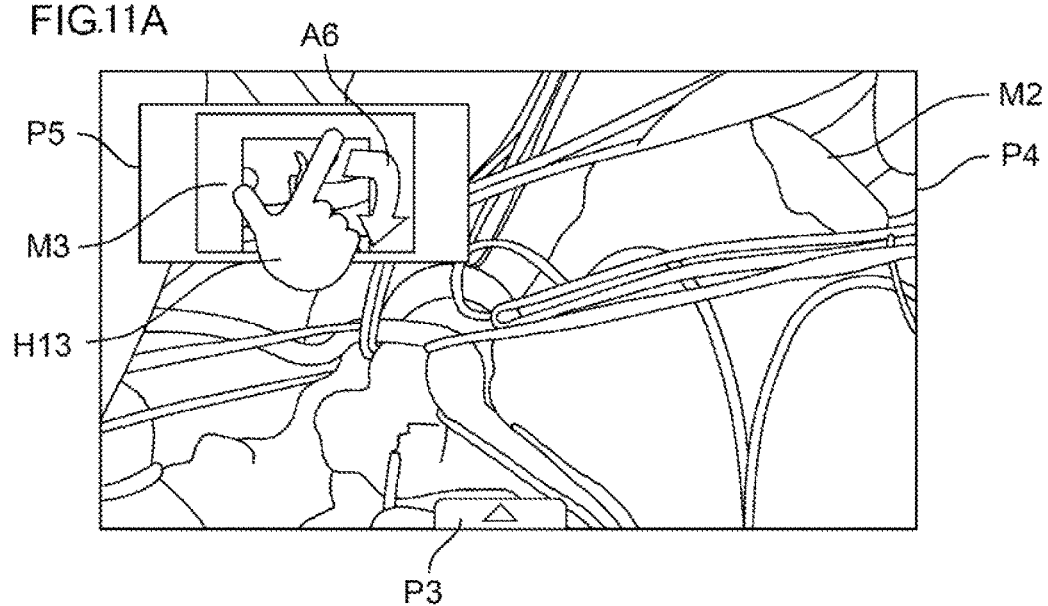
FIGS. 11A and 11B are schematic drawings illustrating a method of manipulation on the touch panel.

FIG. 11A illustrates an exemplary operation of rotating the two touched points, which are given on the video M3 displayed on the sub-screen P5 (action depicted by an arrow A6 and a finger-shaped pointer H13). This sort of operation will be referred to as "rotating operation" in this embodiment.

Upon acceptance of such rotating operation by the touch panel 140, the work station 120 allows the sub-screen P5 to rotate the display position of the video M3, being displayed thereon, 90° in the direction of rotating; operation. For an exemplary case illustrated in FIG. 11A where the rotating operation of the video M3 being displayed on the sub-screen P5 is given clockwise, the video M3 will appear in the sub-screen P5 in a 90° clockwise rotation (see FIG. 11B). A finger-shaped pointer H14 illustrated in FIG. 11B depicts that the two touch position have been rotated clockwise from the two touch positions indicated by the finger-shaped pointer H13.

Upon acceptance of such rotating operation, a status icon ST2 indicating that the video is being rotated appears at a corner of the sub-screen P5. This is an expedient for those who do not take part in the rotating operation (for example, viewers of the monitor 150 on which the video is displayed in synchronization with the touch panel 140), notifying that the video M3 is displayed in a rotation mode.

Figure 11B:
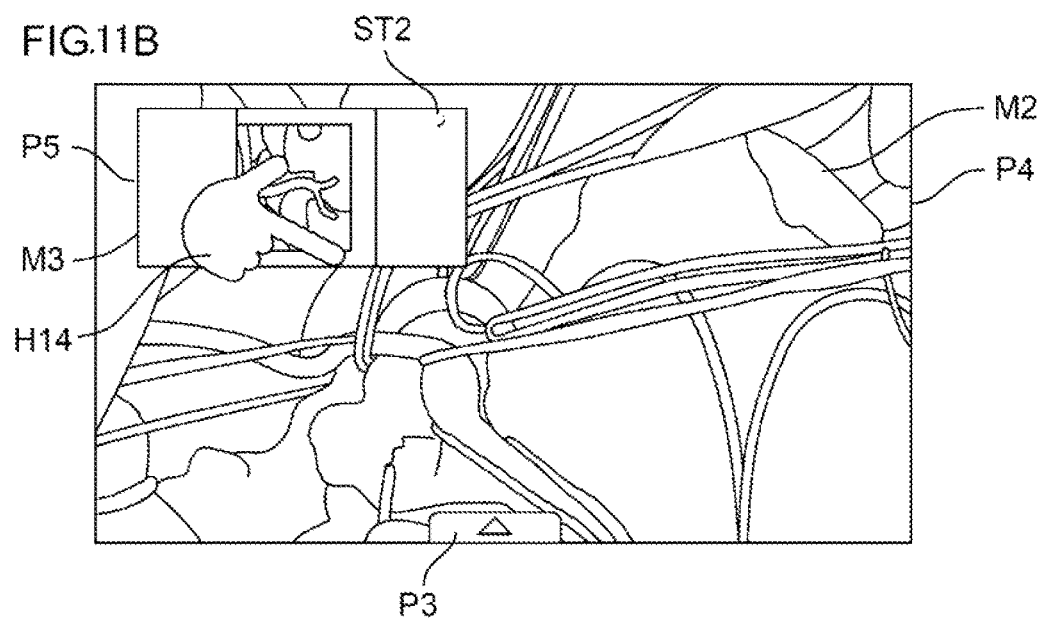

Although the above description making reference to FIGS. 11A and 11B dealt with an exemplary case where the video M3, being displayed on the sub-screen P5, is rotated by the rotating operation, there may be another design in which the video M2, being displayed on the main screen P4, is rotatable by the same rotating operation.

Although the above description, making reference to FIGS. 11A and 11B, dealt with an exemplary case where the video M3, being displayed on the sub-screen P5, is rotated clockwise, the video M3 may be rotated 90° counterclockwise, when the touch panel 140 accepts a counterclockwise rotating operation.

Although the above description, making reference to FIGS. 11A and 11B, dealt with an exemplary case where the video M3 was rotated 90° to be displayed on the sub-screen P5 after a single time of acceptance of the rotating operation by the touch panel 140, the video M3 may further be rotated 90° every time the rotating operation is accepted by the touch panel 140. More specifically, the video M3 may be rotated 180° as a result of acceptance of the rotating operation repeated twice, may be rotated 270° as a result of acceptance of the rotating operation repeated three times, and may be rotated 360° (original position) as a result of acceptance of the rotating operation repeated four times.

To summarize, the display processes based on the individual operations (pinch operation, drag operation, and rotating operation) that are made on the sub-screen, needing such two-point touching as described above with reference to FIG. 9A to FIG. 11B, are as follows.

The work station 120 can allow the touch panel 140 and the monitor 150 to display the video thereon, while dividing the display area of each of them into the main screen, and the sub-screen overlaid on the main screen, and, when the video is displayed on the sub-screen of the touch panel 140, can allow the sub-screen to change the display mode thereof, in response to an operation made on the sub-screen. The work station 120 at this time distributes the video, being displayed on the sub-screen of the touch panel 140, to the monitor 150, and allows the monitor 150 to display it on the sub-screen thereof, enabling that a change in the display mode in response to the operation made on the sub-screen of the touch panel 140 is reflected in the display mode of the sub-screen of the monitor 150 (See, e.g., FIG. 2A and FIG. 2B).

For example, in response to the pinch operation made on the sub-screen of the touch panel 140, the video being displayed therein may be zoomed in/out while keeping the contour size of the sub-screen unchanged, and, corresponding to the zooming in/out of the video on the sub-screen of the touch panel 140 in response to the pinch operation made thereon, the video being displayed on the sub-screen of the monitor 150 may be zoomed in/out while keeping the contour size of the sub-screen unchanged.

Alternatively, in response to the drag operation made on the sub-screen of the touch panel 140, the display position of the video being displayed on the sub-screen may be moved while keeping the display position in the sub-screen unchanged, and, corresponding to the movement of the display position of the video on the sub-screen of the touch panel 140 in response to the pinch operation made thereon, the display position of the video being displayed on the sub-screen of the monitor 150 may be moved, while keeping the display position on the sub-screen unchanged.

Still alternatively, in response to the rotating operation made on the sub-screen of the touch panel 140, the video being displayed on the sub-screen may be rotated while keeping the display angle of the sub-screen unchanged, and, corresponding to the rotation of the display angle of the video on the sub-screen of the touch panel 140 in response to the operation made thereon, the video being displayed on the sub-screen of the monitor 150 may be rotated while keeping the display angle of the sub-screen unchanged.

The individual operations made on the sub-screen, needing such two-point touching as described above with reference to FIG. 9A to FIG. 11B, are also applicable to the main screen. That is, when the video is displayed on the main screen of the touch panel 140, the work station 120 can allow the main screen to change the display mode thereof, in response to an operation made on the main screen. The work station 120 at this time distributes the video, being displayed on the main screen of the touch panel 140, to the monitor 150, and allows the monitor 150 to display it on the main screen thereof, enabling that a change in the display mode in response to the operation made on the main screen of the touch panel 140 is reflected in the display mode of the main screen of the monitor 150.

For example, the video being displayed on the main screen may be zoomed in/out, in response to the pinch operation made on the main screen of the touch panel 140, and, corresponding to the zooming in/out of the video on the main screen of the touch panel 140 in response to the pinch operation made thereon, the video being displayed on the main screen of the monitor 150 may be zoomed in/out.

Alternatively in response to the drag operation made on the main screen of the touch panel 140, the display position of the video, being displayed on the main screen of the touch panel 140, may be moved, and corresponding to the movement of the display position of the video on the main screen of the touch panel 140 in response to the pinch operation made thereon, the display position of the video being displayed on the main screen of the monitor 150 may be moved.

Still alternatively, in response to the rotating operation made on the main screen of the touch panel 140, the video being displayed on the main screen may be rotated, and, corresponding to the rotation of the display angle of the video on the main screen of the touch panel 140 in response to the operation made thereon, the video being displayed on the main screen of the monitor 150 may be rotated.

Besides the operations described above, the touch panel 140 can also accept the operations below.

For example, with the main screen P4 and the sub-screen P5 displayed on the touch panel 140, upon touching the sub-screen P5 by an operator, the work station 120 allows the sub-screen P5 to display an operation icon I4, an operation icon I5, an operation icon I6, and an operation icon I7 so as to be overlaid on the video M3 being displayed on the sub-screen P5, just like when the video listed in the thumbnail P31 is touched (see FIG. 12A).

When the operation icon I4 is touched in this situation, the work station 120 allows the main screen P4 to replace the video M3, being displayed thereon, with the video M2 to be displayed instead, and allows the sub-screen P5 to replace the video M2, being displayed thereon, with the video M3 to be displayed instead (not illustrated).

When the operation icon I5 is touched in this situation, the work station 120 allows the touch panel 140 to enlarge the video M3 to full screen, regardless of the display mode of the main screen P4 (not illustrated).

When the operation icon I6 is touched in this situation, the work station 120 allows the sub-screen P5 to disappear from above the main screen P4 (not illustrated). That is, the work station 120 allows the touch panel 140 to display the main screen P4 only.

When the operation icon I7 is touched in the scene illustrated in FIG. 12A, the work station 120 allows the touch panel 140 to display the zoom-in panel EX3 beside the sub-screen P5. A finger-shaped pointer H15 in FIG. 12A depicts that the operator touches the operation icon I7.

The zoom-in panel EX3 contains operation icons I8 to I20 (see FIG. 13).

When the operation icon I8 is touched, the work station 120 allows the sub-screen P5 to rotate the video M3, being displayed thereon, 90° clockwise. That is, a process same as that carried out in response to the rotating operation described above will take place. When the operation icon I9 is touched, the work station 120 allows the video M3, being rotated, to return back to the original position. The operation icon I9 can return not only the video M3 having been rotated as a result of the operation made on the operation icon I8, but also the video M3 having been rotated as a result of the rotating operation described above, back to the original position.

When the operation icon I10 is touched, the work station 120 allows the video M3 being displayed on the sub-screen P5 to invert laterally. When the operation icon I11 is touched, the work station 120 allows the video M3 being displayed on the sub-screen P5 to invert vertically. When the operation icon 112 is touched, the work station 120 allows the video M3 being laterally or vertically inverted to return back to the original position.

When the operation icon I13 is touched, the work station 120 allows the sub-screen P5 to increase the brightness (luminance) of the video M3 being displayed thereon, and when the operation icon I14 is touched, work station 120 allows the sub-screen P5 to reduce the brightness of the video M3 being displayed thereon. When the operation icon I15 is touched, the work station 120 allows the video M3, being displayed with the brightness increased or decreased from the reference value, to recover its reference value. A numeral that appears between the operation icon I13 and the operation icon I14 represents the brightness of the video M3, where 0 (zero) represents the reference value.

When the operation icon I16 is touched, the work station 120 allows the sub-screen P5 to increase the contrast (light-dark ratio) of the video M3 being displayed thereon, and when the operation icon I17 is touched, the work station 120 allows the sub-screen P5 to reduce the contrast of the video M3 being displayed thereon. When the operation icon I18 is touched, the work station 120 allows the video M3, being displayed with a contrast increased or decreased from the reference value, to recover its reference value. A numeral that appears between the operation icon I16 and the operation icon I17 represents the contrast of the video M3, where 0 (zero) represents the reference value.

When the operation icon I19 is touched, the work station 120 initializes all parameters adjustable on the zoom-in panel EX3 (display angle, display position, inversion, brightness and contrast of the video M3) to the original values. When the operation icon I20 is touched, the work station 120 allows the zoom-in panel EX3 to close (return back to the state shown in FIG. 12A).

Regarding the operation icon I8, among all operation icons illustrated in FIG. 13, the paragraph above described that it activates an operation same as the aforementioned rotating operation. Also operations on other operation icons may be substituted by other simple operations on the touch panel 140 (operations accessible without showing the operation icons). For example, the video M3 being displayed on the sub-screen P5 may be allowed to vary its brightness or contrast, by tracing the edge of the sub-seen P5 (touching a certain point on the edge and moving the finger along the edge).

Although the operation icons illustrated in FIGS. 12A and 12B, and FIG. 13 were those appear on the sub-screen P5 when the operator touches the sub-screen P5, there may be other operational icons separately displayed in the main screen P4 when the operator touches the main screen P4. The operation icons displayed in the main screen P4 are those for changing the display mode of the main screen P4.

Since the display on the touch panel 140 and the monitor 150 may be changed through the operations described above, so that the operator intuitively manipulate the display on the monitor 150 (main screen P1 and sub-screen P2) with improved manipulability.

The above-described operations on the touch panel 140 are mere examples. Operations acceptable on the touch panel 140 in this embodiment, and changes in the display on the touch panel 140 and the monitor 150, resulted from the accepted operations, are not limited to those described above.

The work station 120 preferably allows the monitor 150 to display thereon neither the operation screen P3 nor the operation icons I1 to I20 (including the zoom-in panel EX3 that contains the operation icons I8 to i20). That is, according to a preferred design of the work station 120 and in the process of distributing the video both to the touch panel 140 and the monitor 150, the work station 120 can make the operation screen P3 and the operation icons I1 to i20 attachable only to the video to be distributed to the touch panel 140, but always not attachable to the video to be distributed to the monitor 150.

This is because the operation screen P3 and the operation icons I1 to I20 are mere expedients for accepting the operations, and are intrinsically unnecessary for the monitor 150 that is not a device for accepting operations, and because display of them on the monitor 150 may degrade recognizability of the video.

MODIFIED EXAMPLES OF INVENTION

Having described the embodiment of this invention referring to the attached drawings this invention encompasses various modified embodiments and improved embodiments so long as the objective of this invention will be fulfilled, without being limited by the embodiment described above.

Having described that three display devices—the first monitor 151, the second monitor 157 and the third monitor 153—correspond to the monitor 150 in the aforementioned embodiment, this embodiment is not limited thereto.

For example, this invention may be implemented by an embodiment having one touch panel 140 and one monitor 150, where the distribution device 130 in the aforementioned embodiment is omissible.

Having described that the distribution device 130 in the aforementioned embodiment distributes the video that is output from the work station 120, only to a plurality of display devices (first monitor 151, second monitor 152 and third monitor 153), the distribution device 130 may also distribute the video to devices other than the display devices.

For example, distribution device 130 may distribute the video that is output from the work station 120, to a recording device (not illustrated) for recording the video.

Having exemplified, in the specific examples illustrated in FIG. 4A to FIG. 13, only the case where the operation screen P3 is displayed in an enlarged or reduced manner on the touch panel 140, the operation screen P3 is not always necessarily displayed on the touch panel 140.

For example, when the touch panel 140 accepts an operation of moving the operation screen P3, while being kept toughed by the operator, out of the display screen of the touch panel 140, the work station 120 may make the operation screen P3 hidden. This operation is also referred to as "swipe operation".

Having described the embodiment on the premise of the components illustrated in FIG. 1, the individual components in this invention will suffice if they are formed to implement their functions. The individual components in this invention are therefore not necessarily independent entities, instead allowing that a plurality of components are combined to form a single member, that a single component is composed of a plurality of members, that a certain component is a part of other component, and that a part of a certain component and a part of another component form a common part.

According to this invention, there is provided a medical video display system with improved operability in manipulation regarding display of medical videos.

This embodiment encompasses the technical spirits below:

(1) A medical video display system that includes:
an entry unit through which one, or two or more surgical videos are entered; and
control unit that distributes one video entered through the entry unit and displays it on each of a touch panel and a monitor,
the control unit allows the touch panel, having the video displayed thereon, to display an operation screen or an operation icon for accepting an operation directed to the monitor.

(2) The medical video display system according to (1),
wherein the control unit is designed to enable moving of a display position of the video, being displayed on a part of a display area of the touch panel, in response to a drag operation accepted through the touch panel, and
to enable moving of the display position of the video also on the monitor, corresponding to the moving of the display position of the video in response to the drag operation.

(3) The medical video display system according to (1),
wherein the control unit is designed to enable zooming in/out of the video being displayed on the display area of the touch panel, in response to the drag operation accepted through the touch panel, and,
to enable zooming in/out the video also on the monitor, corresponding to the zooming in/out of the video in response to the drag operation.

(4) The medical video display system according to (1),
wherein the control unit
can allow each of the touch panel and the monitor to display the video thereon, while dividing the display area into a main screen and a sub-screen that is overlaid on the main screen,
can allow the sub-screen of the touch panel to change a display mode thereof, when the video is displayed on the sub-screen, in response to an operation made on the sub-screen, and
distributes the video, being displayed on the sub-screen of the touch panel, to the monitor, and allows the monitor to display it on the sub-screen thereof, enabling that a change in the display mode made on the sub-screen of the touch panel is reflected in the display mode of the sub-screen of the monitor.

(5) The medical video display system according to (4),
wherein the control unit
can allow the main screen of the touch panel to change a display mode thereof, when the video is displayed on the main screen, in response to an operation made on the main screen, and
distributes the video, being displayed on the main screen of the touch panel, to the monitor, and allows the monitor to display it on the main screen thereof, enabling that a change in the display mode made on the main screen of the touch panel is reflected in the display mode of the main screen of the monitor.

(6) The medical video display system according to (4),
wherein the control unit
can allow the touch panel to zoom in/out the video, when displayed on the sub-screen thereof, in response to an operation made on the sub-screen, while keeping the contour size of the sub-screen unchanged, and
can allow the monitor to zoom in/out the video, being displayed on the sub-screen thereof, corresponding to the zooming in/out of the video on the sub-screen of the touch panel in response to a pinch operation made thereon, while keeping the contour size of the sub-screen of the monitor unchanged.

(7) The medical video display system according to (4),
wherein the control unit
can allow the touch panel to move the display position of the video, when displayed on the sub-screen thereof, in response to an operation made on the sub-screen, while keeping the display position of the sub-screen unchanged, and
can allow the monitor to move the display position of the video, being displayed on the sub-screen thereof, corresponding to the moving of the display position of the video on the sub-screen of the touch panel in response to a pinch operation made thereon, while keeping the display position of the sub-screen of the monitor unchanged.

(8) The medical video display system according to (4),
wherein the control unit
can allow the touch panel to rotate the video, when displayed on the sub-screen thereof, in response to an operation made on the sub-screen, while keeping a display angle of the sub-screen unchanged, and
can allow the monitor to rotate the video, being displayed on the sub-screen thereof, corresponding to the rotation of the display angle of the video on the sub-screen of the touch panel in response to an operation made thereon, while keeping the display angle of the sub-screen of the monitor unchanged.

(9) The medical video display system according to (1),
wherein the operation screen that appears on the touch panel contains a thumbnail of the video entered through the entry unit, and
the control unit allows the touch panel to display thereon a video that is selected, by a touch operation accepted by the touch panel, from the videos contained in the thumbnail, separately from the thumbnail, and allows also the monitor to display the selected video.

(10) The medical video display system according to (1), wherein the control unit allow the monitor to display thereon neither the operation screen nor the operation icon.

(11) The medical video display system according to (1), wherein the monitor has a larger display area than the touch panel has.

What is claimed is:

1. A medical video display system comprising:
an entry unit through which one, or two or more surgical videos are entered; and
control unit that distributes one video entered through the entry unit and displays it on each of a touch panel and a monitor,
wherein the control unit allows the touch panel, having the video displayed thereon, to display an operation screen or an operation icon for accepting an operation directed to the monitor,
wherein the control unit allows the monitor to display thereon neither the operation screen nor the operation icon,
wherein the control unit
can allow each of the touch panel and the monitor to display the video thereon, while dividing the display area into a main screen and a sub-screen that is overlaid on the main screen,
can allow the sub-screen of the touch panel to change a display mode thereof, when the video is displayed on the sub-screen, in response to an operation made on the sub-screen, and
distributes the video, being displayed on the sub-screen of the touch panel, to the monitor, and allows the monitor to display it on the sub-screen thereof, enabling that a change in the display mode made on the sub-screen of the touch panel is reflected in the display mode of the sub-screen of the monitor,
wherein the control unit
can allow the main screen of the touch panel to change a display mode thereof, when the video is displayed on the main screen, in response to an operation made on the main screen, and
distributes the video, being displayed on the main screen of the touch panel, to the monitor, and allows the monitor to display it on the main screen thereof, enabling that a change in the display mode made on the main screen of the touch panel is reflected in the display mode of the main screen of the monitor,
wherein the control unit
can allow the touch panel to zoom in/out the video, when displayed on the sub-screen thereof, in response to an operation made on the sub-screen, while keeping a contour size of the sub-screen unchanged, and
can allow the monitor to zoom in/out the video, being displayed on the sub-screen thereof, corresponding to the zooming in/out of the video on the sub-screen of the touch panel in response to a pinch operation made thereon, while keeping the contour size of the sub-screen of the monitor unchanged, and
wherein the control unit
does not allow the sub-screen of the touch panel to change the display mode of the main screen of the touch panel in response to the pinch operation.

2. The medical video display system according to claim 1, wherein the control unit is designed to enable moving of a display position of the video, being displayed on a part of a display area of the touch panel, in response to a drag operation accepted through the touch panel, and to enable moving of the display position of the video also on the monitor, corresponding to the moving of the display position of the video in response to the drag operation.

3. The medical video display system according to claim 1, wherein the control unit is designed to enable zooming in/out of the video being displayed on the display area of the touch panel, in response to a drag operation accepted through the touch panel, and, to enable zooming in/out the video also on the monitor, corresponding to the zooming in/out of the video in response to the drag operation.

4. The medical video display system according to claim 1, wherein the operation screen that appears on the touch panel contains a thumbnail of the video entered through the entry unit, and
the control unit allows the touch panel to display thereon a video that is selected, by a touch operation accepted by the touch panel, from the videos contained in the thumbnail separately from the thumbnail, and allows also the monitor to display the selected video.

5. The medical video display system according to claim 1, wherein the monitor has a larger display area than the touch panel has.

6. A medical video display system comprising:
an entry unit through which one, or two or more surgical videos are entered; and
control unit that distributes one video entered through the entry unit and displays it on each of a touch panel and a monitor,
wherein the control unit allows the touch panel, having the video displayed thereon, to display an operation screen or an operation icon for accepting an operation directed to the monitor,
wherein the control unit allows the monitor to display thereon neither the operation screen nor the operation icon, and
wherein the control unit
can allow each of the touch panel and the monitor to display the video thereon, while dividing the display area into a main screen and a sub-screen that is overlaid on the main screen,
can allow the sub-screen of the touch panel to change a display mode thereof, when the video is displayed on the sub-screen, in response to an operation made on the sub-screen, and
distributes the video, being displayed on the sub-screen of the touch panel, to the monitor, and allows the monitor to display it on the sub-screen thereof, enabling that a change in the display mode made on the sub-screen of the touch panel is reflected in the display mode of the sub-screen of the monitor,
wherein the control unit
can allow the main screen of the touch panel to change a display mode thereof, when the video is displayed on the main screen, in response to an operation made on the main screen, and
distributes the video, being displayed on the main screen of the touch panel, to the monitor, and allows the monitor to display it on the main screen thereof, enabling that a change in the display mode made on the main screen of the touch panel is reflected in the display mode of the main screen of the monitor, and
wherein the control unit
can allow the touch panel to move a display position of the video, when displayed on the sub-screen thereof, in response to an operation made on the sub-screen, while keeping the display position of the sub-screen unchanged, and
can allow the monitor to move the display position of the video, being displayed on the sub-screen thereof, corresponding to the moving of the display position of the video on the sub-screen of the touch panel in response to a pinch operation made thereon, while keeping the display position of the sub-screen of the monitor unchanged, and wherein the control unit
does not allow the sub-screen of the touch panel to change the display mode of the main screen of the touch panel in response to the pinch operation.

7. A medical video display system comprising:
an entry unit through which one, or two or more surgical videos are entered; and
control unit that distributes one video entered through the entry unit and displays it on each of a touch panel and a monitor,
wherein the control unit allows the touch panel, having the video displayed thereon, to display an operation screen or an operation icon for accepting an operation directed to the monitor,
wherein the control unit allows the monitor to display thereon neither the operation screen nor the operation icon,
wherein the control unit
can allow each of the touch panel and the monitor to display the video thereon, while dividing the display area into a main screen and a sub-screen that is overlaid on the main screen,
can allow the sub-screen of the touch panel to change a display mode thereof, when the video is displayed on the sub-screen, in response to an operation made on the sub-screen, and
distributes the video, being displayed on the sub-screen of the touch panel, to the monitor, and allows the monitor to display it on the sub-screen thereof, enabling that a change in the display mode made on the sub-screen of the touch panel is reflected in the display mode of the sub-screen of the monitor,
wherein the control unit
can allow the main screen of the touch panel to change a display mode thereof, when the video is displayed on the main screen, in response to an operation made on the main screen, and
distributes the video, being displayed on the main screen of the touch panel, to the monitor, and allows the monitor to display it on the main screen thereof, enabling that a change in the display mode made on the main screen of the touch panel is reflected in the display mode of the main screen of the monitor,
wherein the control unit
can allow the touch panel to rotate the video, when displayed on the sub-screen thereof, in response to an operation made on the sub-screen, while keeping a display angle of the sub-screen unchanged, and
can allow the monitor to rotate the video, being displayed on the sub-screen thereof, corresponding to the rotation of the display angle of the video on the sub-screen of the touch panel in response to an operation made thereon, while keeping the display angle of the sub-screen of the monitor unchanged, and
wherein the control unit
does not allow the sub-screen of the touch panel to change the display mode of the main screen of the touch panel in response to the operation.

* * * * *